(12) United States Patent
Shen

(10) Patent No.: US 6,746,708 B2
(45) Date of Patent: Jun. 8, 2004

(54) DISPOSABLE PLATE ELECTRODE WITH BIOLOGICAL ACTIVE FILM AND MANUFACTURE METHOD THEREOF

(76) Inventor: Thomas Y. Shen, 2F, No. 1, Alley 3, Lane 56, Sec. 4 Ming-Shen E Rd., Taipei (TW)

( * ) Notice: Subject to any disclaimer, the term of this patent is extended or adjusted under 35 U.S.C. 154(b) by 434 days.

(21) Appl. No.: 09/852,048

(22) Filed: May 10, 2001

(65) Prior Publication Data

US 2001/0024804 A1 Sep. 27, 2001

Related U.S. Application Data

(62) Division of application No. 09/348,824, filed on Jul. 8, 1999, now Pat. No. 6,413,394.

(51) Int. Cl.⁷ .............................. B05D 1/32; B05D 5/12
(52) U.S. Cl. .................... 427/2.11; 427/2.1; 427/2.13; 427/58; 427/96; 427/207.1; 427/208.6; 427/258; 427/402; 427/414; 427/415
(58) Field of Search ............................. 427/2.1, 2.11, 427/2.13, 58, 96, 207.1, 208.6, 258, 402, 414, 415

(56) References Cited

U.S. PATENT DOCUMENTS

| | | | | |
|---|---|---|---|---|
| 5,288,636 A | * | 2/1994 | Pollmann et al. | 204/403.14 |
| 5,770,028 A | * | 6/1998 | Maley et al. | 204/403.11 |
| 5,958,201 A | | 9/1999 | Craig et al. | 204/418 |
| 6,241,862 B1 | * | 6/2001 | McAleer et al. | 204/403.05 |
| 6,258,230 B1 | * | 7/2001 | Shen et al. | 204/403.02 |

* cited by examiner

Primary Examiner—Shrive P. Beck
Assistant Examiner—Jennifer Kolb Michener
(74) Attorney, Agent, or Firm—Bacon & Thomas

(57) ABSTRACT

A manufacture method for forming a disposable plate electrode with biological active film is used to cooperate with a biological sensor for analyzing composition and measuring concentration of a test sample according to electric effect resulted from a biochemical reaction. The plate electrode comprises at least an electrode portion for transmission of the electric effect as well as a biological active film that reacts with the test sample chemically or biochemically. The biological active film contains a carrier layer (cellulose, for example) for adsorbing and keeping the biological active substance (enzyme, for example), which, the carrier layer, can change the electrode portion from hydrophobic into hydrophilic and protect the biological active substance against impairment during relatively higher temperature drying process. The method for forming a biological active film on the disposable electrode is mainly based on screen printing technique to form a conductive film, an electric insulating layer, a carrier layer, etc, for speedy production and low cost purpose.

14 Claims, 6 Drawing Sheets

DISPOSABLE PLATE ELECTRODE WITH BIOLOGICALACTIVE FILM AND MANUFACTURE METHOD THEREOF

This application is a divisional of application Ser. No. 09/348,824, filed Jul. 8, 1999, now U.S. Pat. No. 6,413,394 of which the entire disclosure of the pending, prior application is hereby incorporated by reference.

BACKGROUND OF THE INVENTION

This invention relates to a disposable plate electrode with biological active film and manufacture method thereof, particularly to a manufacture method that can produce plate electrode speedily and to a disposable plate electrode which is used to cooperate with a biosensor for composition analysis and concentration measurement of a test sample in accordance with the electrical output resulted from biochemical reaction.

The biochemistry analyzer is usually classified into three categories, namely, the wet type analyzer, the dry type analyzer, and the biosensor. Application of a conventional wet type biochemistry analyzer is to mix a test sample with reagent (a chromatic agent is commonly contained) for chemical reaction, then an optical reading device, such as a colorimeter or a spectrophotometer, is used to read color change before and after the reaction. This test way is weak at: a pre-treatment required for the test sample; difficulties in dosing and keeping a reagent valid for a long period; expensive instruments; and unfeasibility for non-professional operation, so that it fits a hospital or an examining center for mass sample analyses better than few quantity or emergency tests.

As to application of the dry type biochemistry analyzer, a test strip is coated on its surface with a chemical reagent, such as an enzyme, or antibody, etc to contact directly and react with the test sample for analysis. Though this test way can save dosing and adding process of the reagent, color of the test strip may be changed due to oxidation to affect color judgment before and after reaction.

The biosensor is composed of a biological element, a thin film element, and a sensor, wherein the biological element is made from biological material with cognizable specialties, such as microbe, cell, tissue, enzyme, antigen, and antibody, etc; the thin film element is usually made from polymeric material and used to fix the biological element and sieve out interference substance; and, the sensor may comprise electrodes, ion selective field effect transistors, thermistors, piezoelectric devices, optical fiber, photoelectric tubes, and sound wave counters, etc., and wherein the hydrogen peroxide electrode is the one most widely used.

Take the biosensor for analyzing blood glucose for instance, glucose is oxidized and fixed on a thin film, which is clad tightly on surface of a pillar hydrogen peroxide electrode, then a polarized potential is applied to the platinum anode and the silver/silver chloride cathode, the hydrogen peroxide produced by oxidation of the glucose will continue to be oxidized to water near surface of the anode, and meanwhile, release electrons. The glucose concentration of the test sample may be calculated according to the released amount of electrons.

The aforesaid pillar electrodes shall require constant refreshment including polishing, film clothing, cleaning, and recalibrating, etc, which may incur cross pollution owing to carelessness in addition to inconvenient implementation, not to mention the high production cost. For eliminating above defects, the U.S. Pat. No. 4,545,382 of Genetics International in UK has disclosed a blood glucose meter "Exactech" which is the first commercially realized example of a plate electrode in this field.

In U.S. Pat. No. 5,120,420—Biosensor and process for preparation thereof, another disclosed biological detecting plate electrode comprises an electrode portion, an insulation layer, a reaction layer, and a test sample bearing space on the reaction layer, wherein a sample inlet port and an gas exhaust port are provided to the bearing space. The reaction layer is formed by coating subsequently CMC (Carboxymethyl Cellulose) water solution on the electrode substrate to form a CMC layer, water solution of GOD (Glucose Oxidase), and then a suspending liquid containing conductive mediator to form a biochemistry reaction portion. Finally, a resin plate and a top plate are used to cover on the substrate to form the sample bearing space and complete thereby the biological detecting plate electrode.

The biochemistry reaction portion of the aforesaid U.S. Pat. No. 5,120,420 is formed in 3 steps, namely:

1. The CMC layer used to improve hydrophobicity of the carbon electrodes.
2. The GOD layer.
3. The conductive mediator layer.

Each step requires drying before completed.

SUMMARY OF THE INVENTION

This invention is proposed to provide a new fabrication process for plate electrode, which is provide at least with an electrode portion used to transmit electrical effect produced from biological reaction; and a biological active layer used to conduct a chemical or biochemical reaction with a test sample. The biological active layer comprises at least 3 portions: an absorptive carrier layer, an enzyme, and a conductive mediator. The carrier is printed on surface of the electrode portion with screen-printing technique and used to suck and sustain the biological active substance (such as enzyme) and the conductive mediator. Also, the carrier can turn the electrode portion from hydrophobic into hydrophilic, and moreover, protect the biological active substance against impairment in relatively high temperature drying process to make a speedy production of the plate electrode become possible.

Another object of this invention is to provide a simplified process for production of the plate electrode, wherein the carrier layer is printed on an insulating substrate of the plate electrode with screen-printing technique.

BRIEF DESCRIPTION OF THE DRAWINGS

For a better understanding to the present invention, together with further advantages or features thereof, at least one preferred embodiment will be elucidated below with reference to the annexed drawings in which.

DETAILED DESCRIPTION OF THE PREFERRED EMBODIMENT

Figure 1:
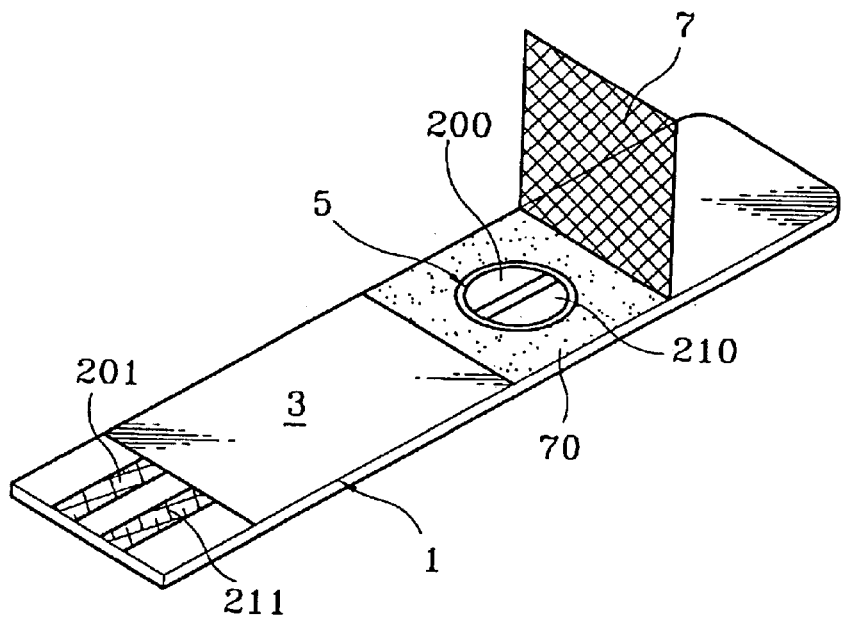
FIG. 1 is an elevational view showing structure of a plate electrode of this invention.
Figure 2:
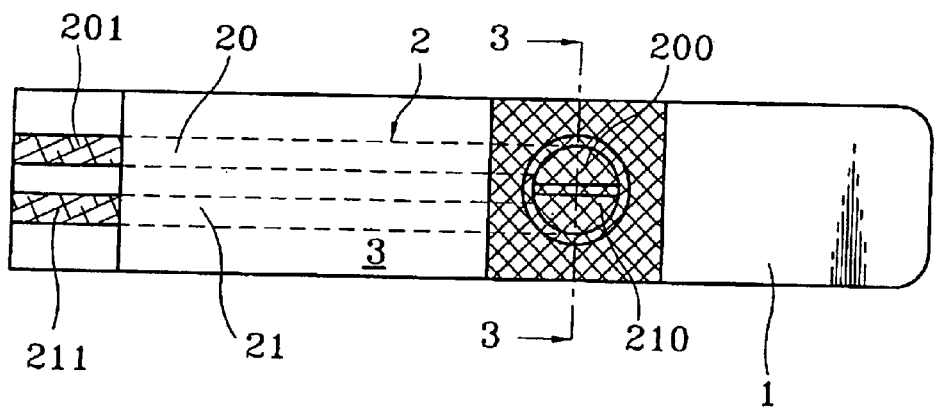
FIG. 2 is a front view showing structure of the plate electrode of this invention.
Figure 3:
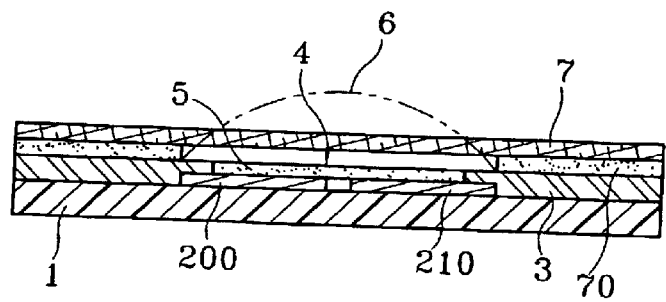
FIG. 3 is a cutaway sectional structure along line III—III in FIG. 2 of the plate electrode of this invention.
Figure 4A:
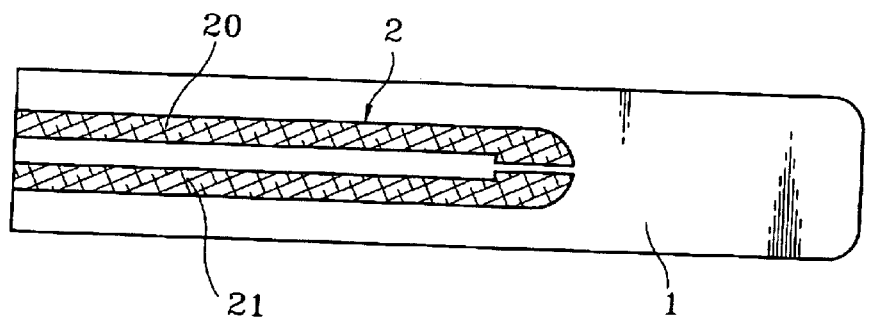
FIGS. 4A through 4H show production flow charts of this invention in preparation steps.
Figure 4B:
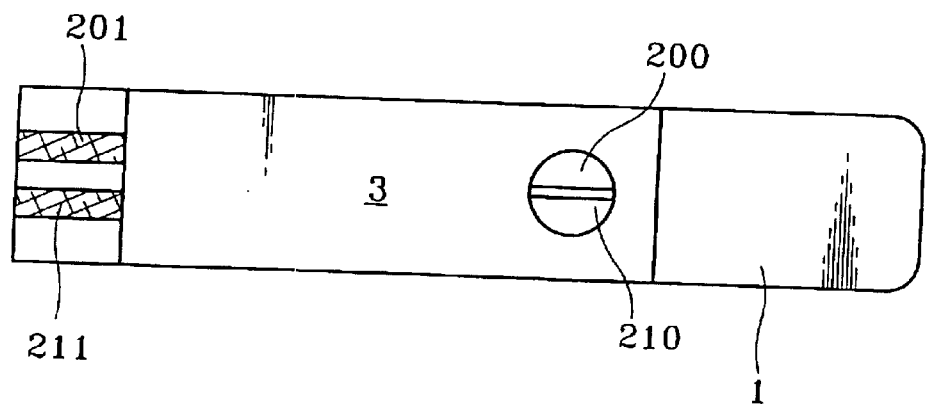
Figure 4C:
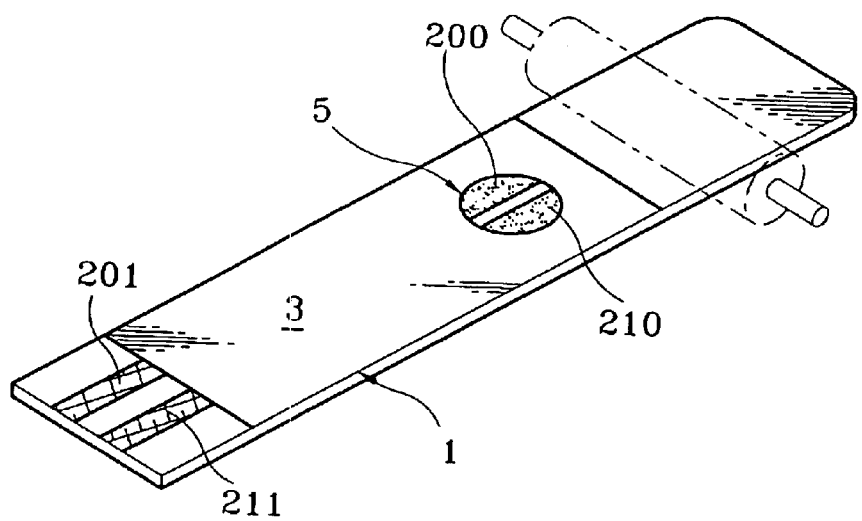
Figure 4D:
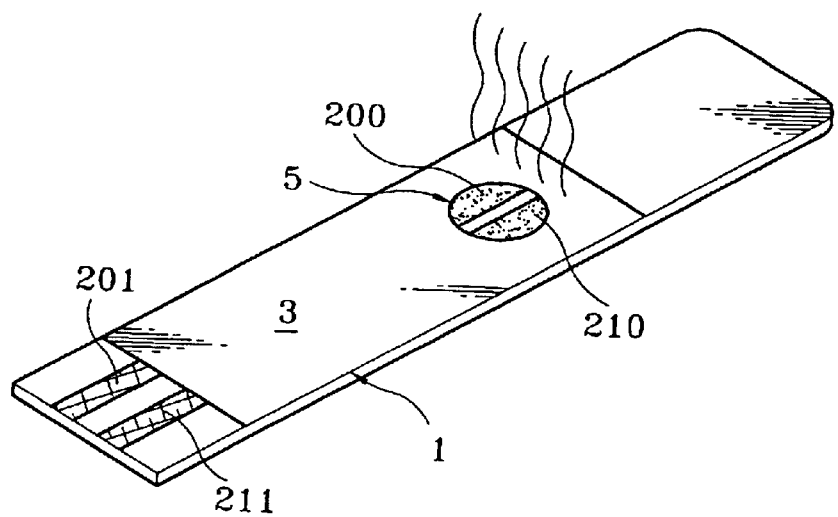
Figure 4E:
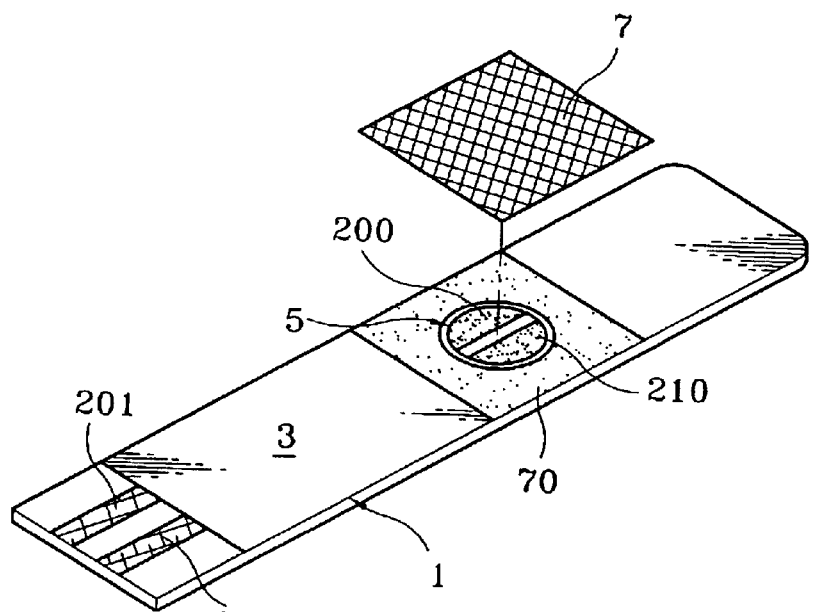
Figure 4F:
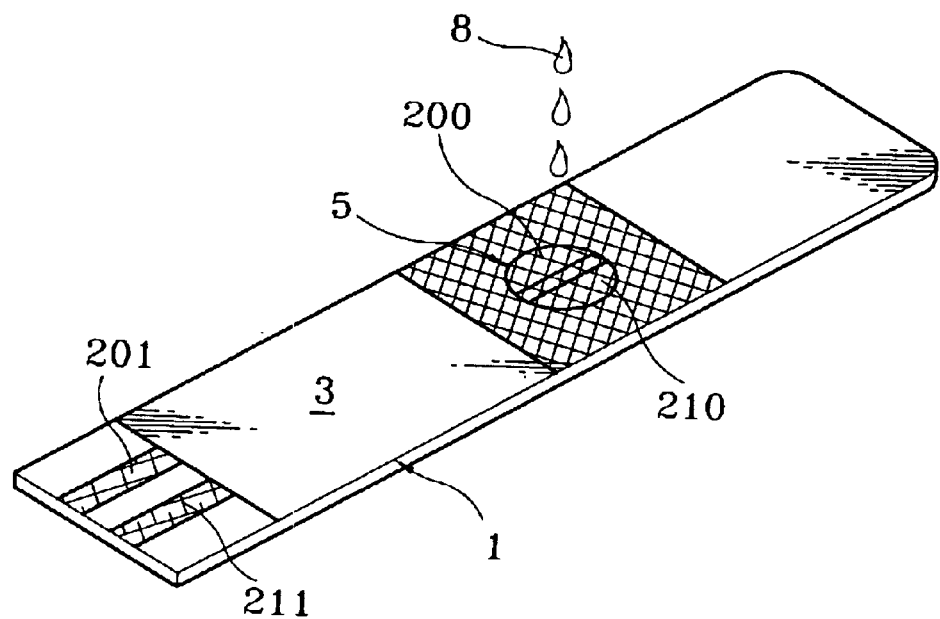
Figure 4G:
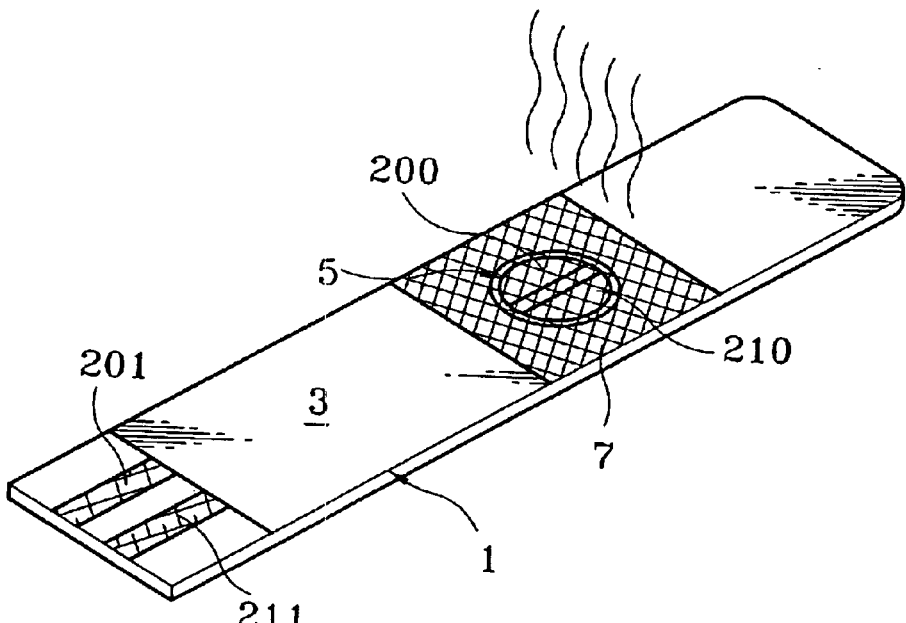
Figure 4H:
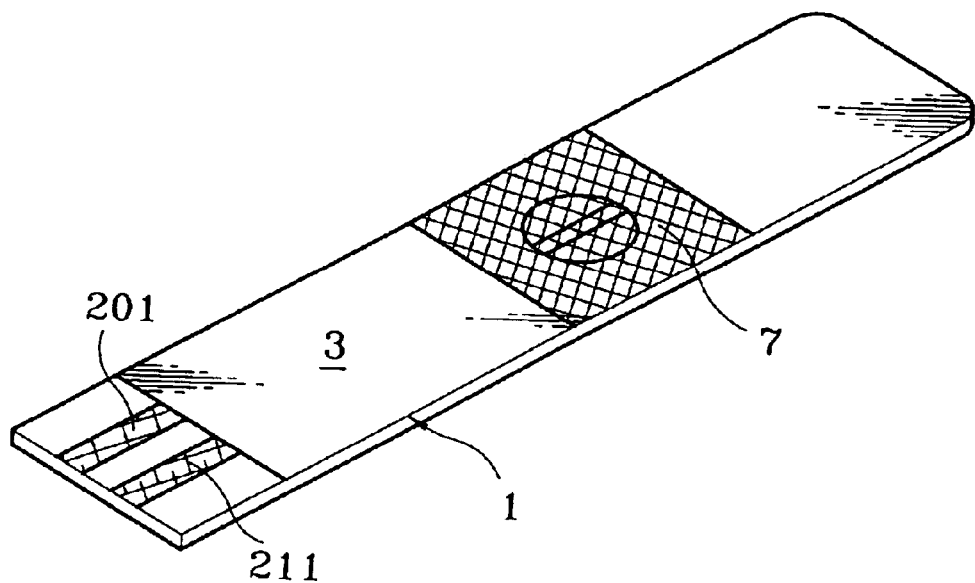

As shown in FIG. 1 and FIG. 2, an approximate strip type plate electrode is advantageous for loading a test sample 6 and suitable for use in the following manufacture method. The plate electrode, according to the cutaway sectional view in FIG. 3, comprises: a strip substrate 1 with plane surface, a conductive film 2 located on one surface of the substrate 1, an electric insulating layer 3 locally covering the conductive film 2, and, a biological active layer 4 covering the bare portion of the conductive film 2, which, the biological active layer 4, doesn't overlap the electric insulating layer 3 thoroughly.

In addition to the plane surface, the foregoing substrate 1 must be meanwhile an electric insulator and a heat resister capable of enduring 40° C.–120° C. heat treatment in order to increase conductivity and adherence of the conductive film 2. The applicable materials for the substrate 1 include PVC (Polyvinyl Chloride), FRP (Fiber Reinforced Plastics, FR-4), Polyester sulfone, BAKELITE, a phenolic resin, PET, PC, glass, or ceramics (CEM-1), etc.

The conductive film 2 comprises at least a pair of separated electrodes, namely, an anode 20 and a cathode 21 to connect with a sensor. One of two bare ends of the anode 20 is a work electrode 200 covered with the biological active layer 4, and the other is an anode coupling 201, wherein the work electrode 200 is used to detect the electric effect induced by chemical or biochemical reaction of the test sample 6, and the anode coupling 201 is used to connect with the sensor as mentioned. As to two bare ends of the cathode 21, one end is a reference electrode 210 covered with the biological active layer 4, and the other is a cathode coupling 211 in arbitrary shape. The reference electrode 210 is used to cooperate with the work electrode 200 for detecting electric effect of the test sample 6, while the cathode coupling 211 is used to connect with the sensor.

The electric insulating layer 3 is coated on the same surface of the substrate 1 at 0.6 mm thick or up without covering the anode coupling 201, the cathode coupling 211, the work electrode 200, and the reference electrode 210 to form a circular area on the work electrode 200 and the reference electrode 210, namely, the space of biological active layer 4, for placing a biological active substance or the test sample 6.

This invention is characterized by providing a distinguishing biological active layer 4 in order to simplify production process of the plate electrode and also to raise its quality. The biological active layer 4 comprises: a carrier 5 printed on the work electrode 200 and the reference electrode 210 by screen-printing technique, a net protector 7 shading on the work electrode 200 and the reference electrode 210, as well as the biological active substance adsorbed by the carrier 5, and the conductive mediator.

The aforesaid carrier 5 is a blended paste for screen-printing, and the ingredients thereof may include:

1. Microcrystalline cellulose with grain size at 100 μm down, 10~40% adulterated.
2. High molecule polymer with 10~25% adulterated, such as PVA (Polyvinyl alcohol), PVP (Polyvinyl pyrrolidone), PEG (Polyethylene glycol), or gelatin. Each single item or blended may be used.
3. Salt adulterated at 1~5%, such as Dibasic potassium phosphate, Potassium biphosphate, and Citric acid. The salt is used to adjust pH value and serve as a buffer solution. The proper range of pH value is 4.5~9.0.
4. Water. Pure water undergone at least one time distillation would be a must.

Embodiment 1:

| | |
|---|---:|
| Microcrystalline cellulose (grain size 20~100 μm) | 20% |
| PVA | 3.5% |
| PVP | 2.8% |
| PEG | 12% |
| Gelatin | 2.1% |
| Dibasic potassium phosphate | 0.7% |
| Citric acid | 1.5% |
| Water | 57.4% |

Embodiment 2:

| | |
|---|---:|
| Microcrystalline cellulose (grain size 20 μm down) | 35% |
| PVA | 13% |
| PVP | 7% |
| Dibasic potassium phosphate | 0.7% |
| Citric acid | 1.5% |
| Water | 42.8% |

Embodiment 3:

| | |
|---|---:|
| Microcrystalline cellulose (grain size 20 μm in average) | 21.2% |
| PEG | 19.8% |
| Dibasic potassium phosphate | 0.7% |
| Citric acid | 1.5% |
| Water | 56.8% |

Embodiment 4:

| | |
|---|---:|
| Microcrystalline cellulose (grain size 20 μm in average) | 21.2% |
| PVP | 13.4% |
| PEG | 0.3% |
| Dibasic potassium phosphate | 0.04% |
| Potassium biphosphate | 0.1% |
| Water | 64.96% |

The carrier 5 is coated on surface of the circular area of the work electrode 200 and the reference electrode 210 for adsorbing a biological active substance and conductive mediator to change the carbon electrodes from hydrophobic into hydrophilic for strengthening adsorption of the test sample and to assure the biological active substance will not be impaired in relatively high temperature drying process, so that the yield of the plate electrode may be raised up. The biological active substance means immobilized or unimmobilized enzyme (such as Glucose Oxidase), antigen, antibody, microbe cell, and cell or tissue of animals or plants, which possess biologically discriminative constituents, for use to react with a test sample (biological tissue such as blood) chemically or biochemically. The conductive mediator (such as potassium ferricyanide, quinones) at content ratio 2~10% is used to receive the electrons released from the reaction between an enzyme and a test sample, which, the electrons, will be transmitted to the sensor via a conductor to transfer into concentration of the test sample.

The biological active substance must be mixed with the conductive mediator, the composition is listed as the following:

1. Enzyme, such as Glucose Oxidase with dosage 200 U~1200 U/ml.

2. Enzyme protector with dosage 0.1~1%, including: albumin, dextrin, dextran, or amino acid, which can be used independently, or in blended.
3. Conductive mediator with dosage 2~10%, such as Potassium ferricyanide.
4. Phosphate buffer solution at pH 4.8~7.5.

| Embodiment 5: | |
| --- | --- |
| Glucose Oxidase | 0.63% |
| Albumin | 0.5% |
| Potassium ferricyanide | 6% |
| Phosphate buffer solution at pH 5.0 | 92.87% |

| Embodiment 6: | |
| --- | --- |
| Glucose Oxidase | 0.45% |
| Albumin | 0.5% |
| Dextran | 0.01% |
| Potassium ferricyanide | 4.8% |
| Phosphate buffer solution at pH 7.4 | 94.24% |

| Embodiment 7: | |
| --- | --- |
| Glucose Oxidase | 0.63% |
| Albumin | 0.5% |
| Glutamic acid | 0.3% |
| Potassium ferricyanide | 6% |
| Phosphate buffer solution at pH 7.0 | 92.57% |

| Embodiment 8: | |
| --- | --- |
| Glucose Oxidase | 0.21% |
| Dextrin | 0.39% |
| Glutamic acid | 0.3% |
| Potassium ferricyanide | 3.8% |
| Phosphate buffer solution at pH 5.1 | 95.3% |

As shown in FIG. 4A through FIG. 4H—the production flow charts of this invention, the procedure includes the following steps:

1. Please refer to FIG. 4A. To print at least one layer conductive film 2 with screen printing technique including at least an anode and a cathode. The material of the conductive film 2 can be a carbon paste, silver plasma, mixed plasma of carbon and silver, volatile graphite, or copper paste, which can be used independently or in pack (for example, printing the carbon paste after the silver plasma), then heated at 40° C.~120° C. for drying.
2. Please refer to FIG. 4B. To print an electric insulating layer 3 at least in 0.6 mm thick on the same face with the printed conductive film 2 by using screen printing technique, except some bare area reserved for forming the anode coupling 201, cathode coupling 211, work electrode 200, and reference electrode 210. A circular area formed by the work electrode 200 and the reference electrode 210 is called the area of biological active layer.
3. Please refer to FIG. 4C. To print a layer of the cellulose carrier on the circular area of the biological active layer with screen printing technique.
4. Please refer to FIG. 4D. To dry the carrier 5 in room temperature (20° C.~30° C.).
5. Please refer to FIG. 4E. To coat the surface surrounding the circular area of the biological active layer with glue 70 and have the net protector 7 adhered to cover the carrier 5 as mentioned in step 3.
6. Please refer to FIG. 4F. To drip the buffer solution 8 containing the biological active substance and conductive mediator into the carrier 5 in the circular area, where the buffer solution 8 will be absorbed by cellulose of the carrier 5.
7. Please refer to FIG. 4G. To dry the plate electrode made according to step 6 in ambient temperature at 40° C.~60° C. to complete the manufacture process as shown in FIG. 4-H.

From above description, it is understood that this invention provides a relatively speedy manufacture process for plate electrode by virtue of coating the cellulose layer of carrier on the biological active layer to adsorb the biological substance and conductive mediator, so that the work electrode and the reference electrode can be changed from hydrophobic into hydrophilic, and the biological substance can be protected against impairment in subsequent manufacture process, and moreover, the screen printing method facilitates a high production yield.

Although, this invention has been described in terms of preferred embodiments, it is apparent that numerous variations and modifications may be made without departing from the true spirit and scope thereof, as set forth in the following claims.

What is claimed is:

1. A manufacture method for forming a biological active layer on a disposable plate electrode, comprising:
    a. using screen printing technique to print at least one conductive film which comprises at least an anode electrode and a cathode electrode on a surface of a substrate and drying thereof at a temperature ranging from 40 to 120 degree Celsius;
    b. using screen printing technique to print an electric insulating layer on the conductive film except selected areas which remain bare and are reserved for forming an anode coupling, a cathode coupling, a work electrode, a reference electrode, and a circular area for the biological active layer which consists of the work electrode and the reference electrode;
    c. using screen printing technique to print a layer of cellulose carrier on the circular area and drying thereof at a room temperature ranging from 20 to 30 degree Celsius;
    d. disposing an adhesive layer at the periphery of the circular area and adhering to thereon a layer of net protector for covering the biological active layer thereunder; and
    e. dripping water solution which contains a biological active substance and a conductive mediator on the surface of the carrier and drying thereof in an ambience at a temperature ranging from 40 to 60 degree Celsius for completing the disposable plate electrode.

2. The manufacture method of claim 1, wherein the substrate is selected from a group consisting of polyvinyl chloride board, Fiber Reinforced Plastics, Polyester suphone, a phenolic resin, PET, Printed Circuit Board, glass, and ceramics.

3. The manufacture method of claim 1, wherein the carrier is a blended paste for screen printing use and is composed of microcrystalline cellulose, high molecule polymer, salt and water.

4. The manufacture method of claim 3, wherein the microcrystalline cellulose has particle size less than 100 μm and is adulterated from 10 % to 40 % by weight.

5. The manufacture method of claim 3, wherein the high molecule polymer is adulterated from 10 % to 25 % by weight and is selected from the group consisting of polyvinyl alcohol, polyvinyl pyrrolidone, Polyethylene glycol, gelatin, and mixtures thereof.

6. The manufacture method of claim 3, wherein the salt is adulterated from 1 % to 5 % by weight for adjusting pH value of the water and serving as a buffer solution, and is selected from the group consisting of Dibasic potassium phosphate, Potassium biphosphate, and Citric acid, the pH value ranging from pH 4.5 to pH 9.0.

7. The manufacture method of claim 3, wherein the water is pure water obtained by distilling at least once.

8. The manufacture method of claim 1, wherein the biological active substance is an immobilized or an unimmobilized substance which possess biological cognizable specialties for use to contact a test sample of a biological tissue included blood for generating chemical or biochemical reaction and is selected from the group consisting of enzyme, antigen, antibody, microbe cell, animal or plant cell, and animal or plant tissue.

9. The manufacture method of claim 1, wherein the conductive mediator is for receiving electrons released after reaction of an enzyme and a test sample, and transmitting the electrons through an electrode conductor to a sensor for converting to sample concentration, and is Potassium Ferricyanide adulterated from 2 % to 10 % by weight.

10. The manufacture method of claim 8, wherein the biological active substance is blended with the conductive mediator before use and composes of substances selected from the group consisting of enzyme, enzyme protector, conductive mediator, and phosphate buffer solution.

11. The manufacture method of claim 10, wherein the enzyme includes glucose oxidase and being adulterated in a range from 200 U/ml to 1200 U/ml.

12. The manufacture method of claim 10, wherein the enzyme protector is selected from the group consisting of albumin, dextrin, dextran, and amino acid, and mixtures thereof, and is adulterated in a range from 0.1 % to 1 % by weight.

13. The manufacture method of claim 10, wherein the conductive mediator is potassium ferricyanide adulterated in a range from 2 % to 10 % by weight.

14. The manufacture method of claim 10, wherein the phosphate buffer solution has pH value ranging from pH 4.8 to pH 7.5.

* * * * *